US006832044B2

United States Patent
Doi et al.

(10) Patent No.: US 6,832,044 B2
(45) Date of Patent: Dec. 14, 2004

(54) IRIS IMAGING APPARATUS

(75) Inventors: Makoto Doi, Ishikawa-gun (JP); Jouji Wada, Yokohama (JP); Ken Ikoma, Yokohama (JP); Tomoyoshi Nakaigawa, Yokohama (JP); Toshiharu Aikawa, Yokohama (JP); Kouji Ooi, Kanazawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/425,419

(22) Filed: Apr. 29, 2003

(65) Prior Publication Data
US 2003/0219247 A1 Nov. 27, 2003

(30) Foreign Application Priority Data
Apr. 30, 2002 (JP) .................................. P. 2002-128317

(51) Int. Cl.⁷ .............................................. G03B 29/00
(52) U.S. Cl. ........................... 396/18; 396/427; 348/78; 348/143
(58) Field of Search ..................... 396/18, 427; 348/48, 348/78, 143, 373

(56) References Cited

U.S. PATENT DOCUMENTS 6,320,610 B1 * 11/2001 Van Sant et al. ........... 348/143
6,591,064 B2 * 7/2003 Higashiyama et al. ........ 396/18

FOREIGN PATENT DOCUMENTS

JP 2002-122899 4/2002

* cited by examiner

Primary Examiner—David M. Gray
(74) Attorney, Agent, or Firm—Pearne & Gordon LLP

(57) ABSTRACT

The present invention provides an iris imaging apparatus is configured of a platform; a wide angle camera for imaging an image of a person to be authenticated; wide angle camera lighting devices controlled to emit light when the wide angle camera shoots; a telephoto camera for imaging the enlarged image of the eye of the person to be authenticated; iris lighting devices controlled to emit light when the telephoto camera shoots; first motors for rotating the iris lighting devices and directing the luminous light in the direction of the person to be authenticated; a turning stage mounted with the wide angle camera, the wide angle camera lighting devices, the telephoto camera, the iris lighting devices and the first motors, the turning stage rotatablly mounted on the platform; and a second motor for turning the turning stage. All the components required for the turning operation are mounted on the turning stage.

9 Claims, 4 Drawing Sheets

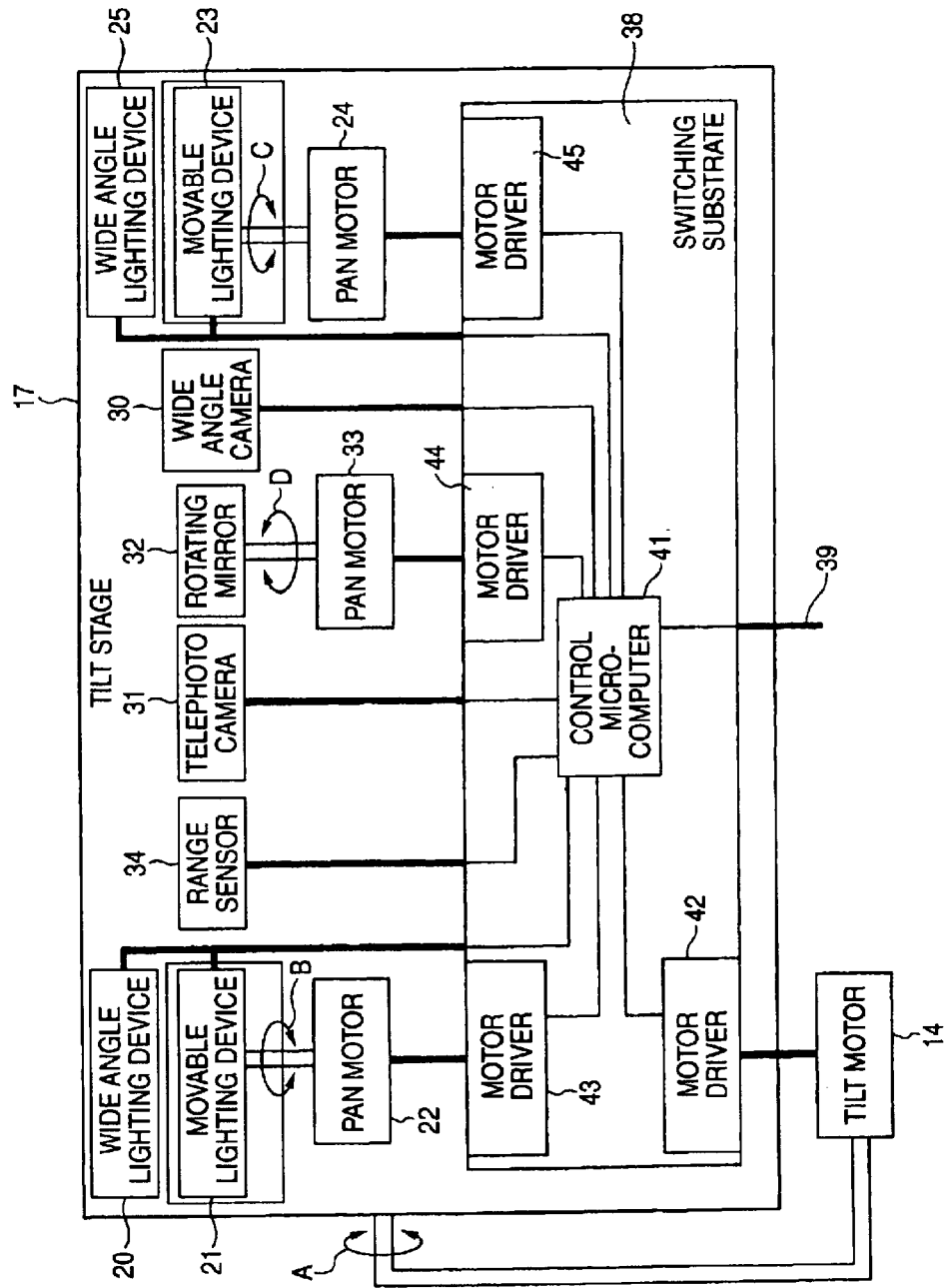

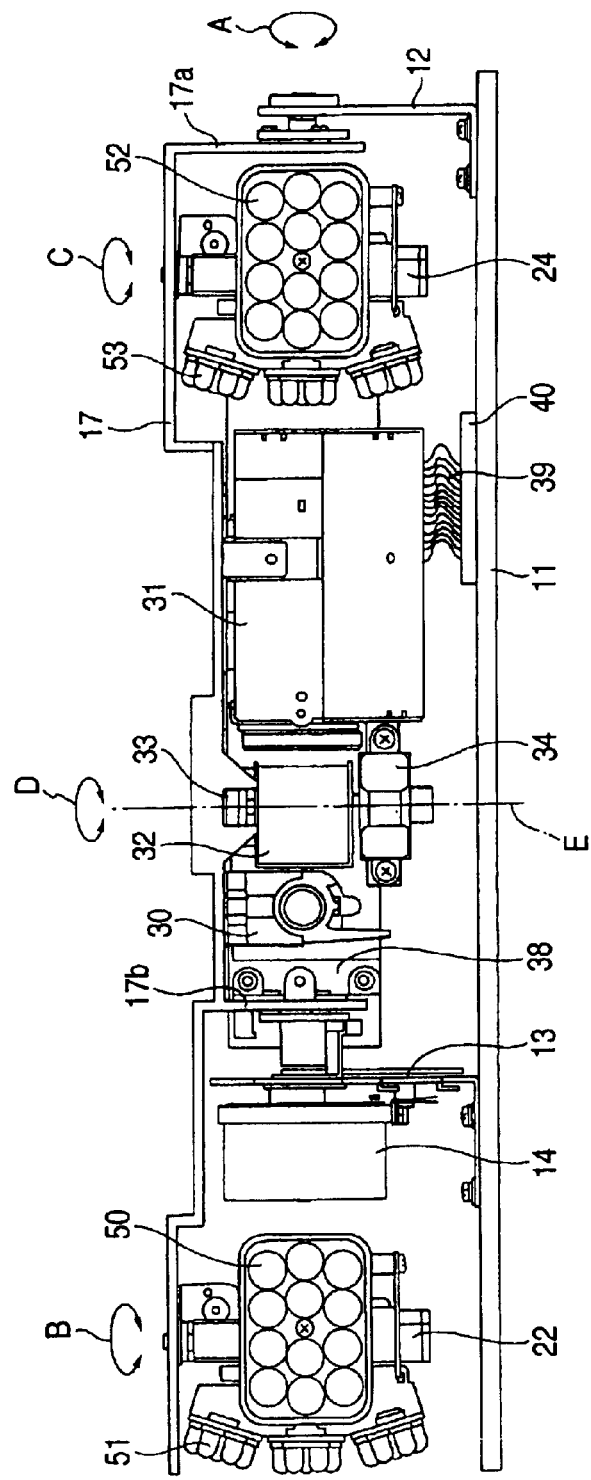

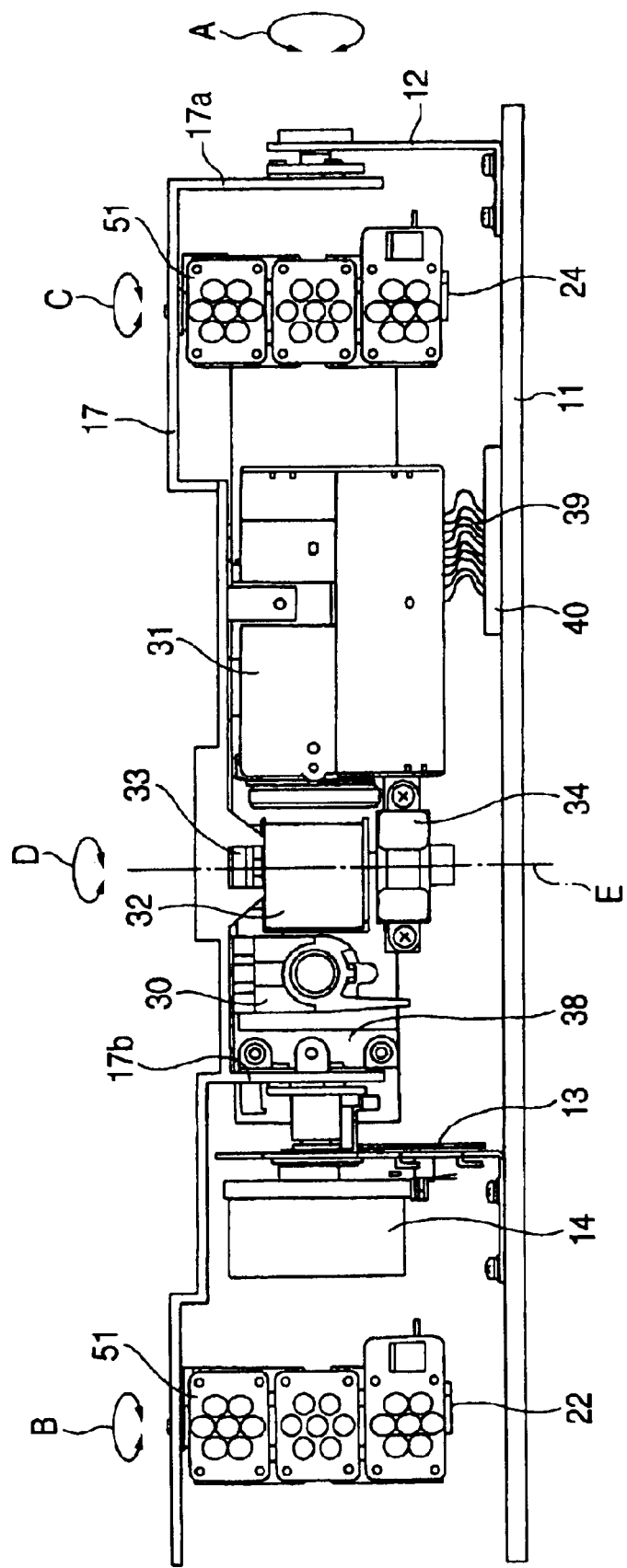

IRIS IMAGING APPARATUS

BACKGROUND OF THE INVENTION

1. Field of the Invention

The present invention relates to an iris imaging apparatus used as a security system, particularly, realizing the reduction in size and in costs.

2. Description of the Related Art

In security systems, a method is known that the iris pattern of individuals is used for authentication. The authentication method using the iris has an advantage that the iris image of a person to be authenticated is imaged by a camera from a remote place without contacting the iris different from fingerprints, which is expected to become popular in future.

An iris imaging apparatus for imaging the iris image needs to capture the iris image of the person to be authenticated at high speed as a sharp image, thus having various drive mechanisms. For example, it needs to image the image of the person to be authenticated by a wide angle camera, to calculate the position of the eye of the person to be authenticated from the image imaged by the wide angle camera, and to set the orientation of a telephoto camera to the position of the eye highly accurately. Therefore, a pan mechanism and a tilt mechanism are disposed in the telephoto camera. In addition, the iris image becomes sharp when it is imaged with the use of near-infrared radiation. Thus, a lighting device for emitting near-infrared radiation is mounted on the iris imaging apparatus, and the lighting device also has the pan mechanism and the tilt mechanism so as to be directed to the position of the eye of the person to be authenticated.

As described above, the iris imaging apparatus of the related art needs to mount many drive mechanisms, which has a problem to cause the obstacles to compactness and low costs.

SUMMARY OF THE INVENTION

The object of the invention is to provide an iris imaging apparatus which is compact at low cost by solving the problem.

To achieve the above object, the invention provides an iris imaging apparatus of the invention comprises a telephoto camera for imaging an enlarged image of an eye of a person to be authenticated, an iris lighting device controlled to emit light when the telephoto camera images the enlarged image, a iris lighting motor for rotating the first iris lighting device to set direction of the iris lighting device to a position of the eye of the person to be authenticated, a platform, and a turning stage rotatablly mounted on the platform, with which the telephoto camera, the first iris lighting device and the iris lighting motor are mounted.

With the configuration, the apparatus can be formed compact at low cost.

Preferably, the iris imaging apparatus further comprises a wide angle camera for imaging an image to determine the position of the eye of the person to be authenticated and a wide angle camera lighting device controlled to emit light when the wide angle camera images, wherein the wide angle camera and the wide angle camera lighting device are mounted with the turning stage. Therefore, the position of the eye of the person to be authenticated can be calculated highly accurately from the image imaged by the wide angle camera to capture the iris image suitable for the iris authentication.

Preferably, the iris imaging apparatus further comprises a controller for controlling the wide angle camera lighting device to emit light and controlling the telephoto camera to image the iris image of the person to be authenticated when an image of the first iris lighting device is reflected in an iris image of the person to be authenticated imaged by the telephoto camera. Therefore, an good iris image can be imaged even when the first iris lighting device cannot be used.

Preferably, a rotation axis of a turn motor for turning the turning stage is set to the turning stage. As all the main components of the iris imaging apparatus are set to the turning stage, electrical wiring on the turning stage can be facilitated.

Preferably, the iris imaging apparatus further comprises a rotating mirror for reflecting an incident light from the eye of the person to be authenticated to the telephoto camera, and a rotating mirror motor for rotating the rotating mirror, wherein the rotating mirror and the rotating mirror motor are mounted with the turning stage, and the telephoto camera is disposed transversely so that the rotation axis of the turning stage is coaxial with an optical axis of the telephoto camera. Therefore, the force required to turn the turning stage is small, and a small motor can turn it.

Preferably, a range sensor for measuring distance to the person to be authenticated is provided to a position below the rotating mirror. Therefore, the distance to the person to be authenticated can be measured accurately to focus the person to be authenticated at higher speed.

Preferably, the range sensor is provided so as to rotate in one piece with the rotating mirror. Therefore, the distance to the person to be authenticated can be measured at low cost.

Preferably, a substrate having a unit for controlling a subject to be electrically controlled is mounted on the turning stage. Therefore, all the subjects to be electrically controlled on the turning stage can be controlled on the turning stage, the electrical wiring for the control system is further facilitated, and the wiring lines are prevented from hindering turning the turning stage.

Preferably, the iris imaging apparatus further comprises a second iris lighting device controlled to emit light when the telephoto camera images the enlarged image, a first position where the first iris lighting device is provided is left side of the turning stage and a second position where the second iris lighting device is provided is right side of the turning stage, and the first position and the second position are asymmetric with respect to an optical axis of the telephoto camera directed to the person to be authenticated. Therefore, the image of the first iris lighting device or the second iris lighting device is prevented from being reflected in the iris image to heighten the probability that an good iris image can be captured. In addition, the number of light emitting diodes used for the first lighting device and the second lighting device can be reduced, which realizes further cost reduction.

To achieve the above object, the invention provides an iris imaging apparatus comprises a platform, a wide angle camera for imaging an image of a person to be authenticated, a wide angle camera lighting device controlled to emit light when the wide angle camera images, a telephoto camera for imaging an enlarged image of an eye of the person to be authenticated, an iris lighting device controlled to emit light when the telephoto camera images the enlarged image, a first motor for rotating the iris lighting device direct luminous light in a direction of the person to be authenticated, a turning stage rotatablly mounted on the platform, with which the wide angle camera, the wide angle camera lighting device, the telephoto camera, the iris lighting device and the first motor are mounted, and a second motor for turning the turning stage. As motor for turning the components mounted on the turning stage in the turning direction can be shared, the number of motors can be reduced. Therefore, the apparatus can be formed compact at low cost.

Preferably, the wide angle camera lighting device and the iris lighting device are arranged side by side adjusted lighting direction by the first motor. According to the configuration, the person to be authenticated can be illuminated efficiently by the wide angle camera lighting device. Therefore, the number of the light emitting diodes use for the wide angle camera lighting device can be reduced.

Preferably, the iris imaging apparatus comprises a controller for controlling the second motor, and the wide angle camera, the wide angle camera lighting device, the telephoto camera, the iris lighting device and the first motor mounted on the turning stage, wherein the controller is mounted with the turning stage. As all the electrical wiring lines routed to the separate components on the turning stage from the controller can be routed on the turning stage, the wiring lines can be prevented from hindering the turning operation of the turning stage.

BRIEF DESCRIPTION OF THE DRAWINGS

FIG. 2 is a block diagram illustrating the electrical system of the iris imaging apparatus in the first embodiment of the invention;

FIG. 3 is a front view illustrating the states that the external panel of the iris imaging apparatus in the second embodiment of the invention is removed and that the lighting devices for illuminating the iris are directed to the person to be authenticated; and FIG. 4 is a front view illustrating the states that the external panel of the iris imaging apparatus in the second embodiment of the invention is removed and that the lighting devices for the wide angle camera are directed to the person to be authenticated.

Figure 1:
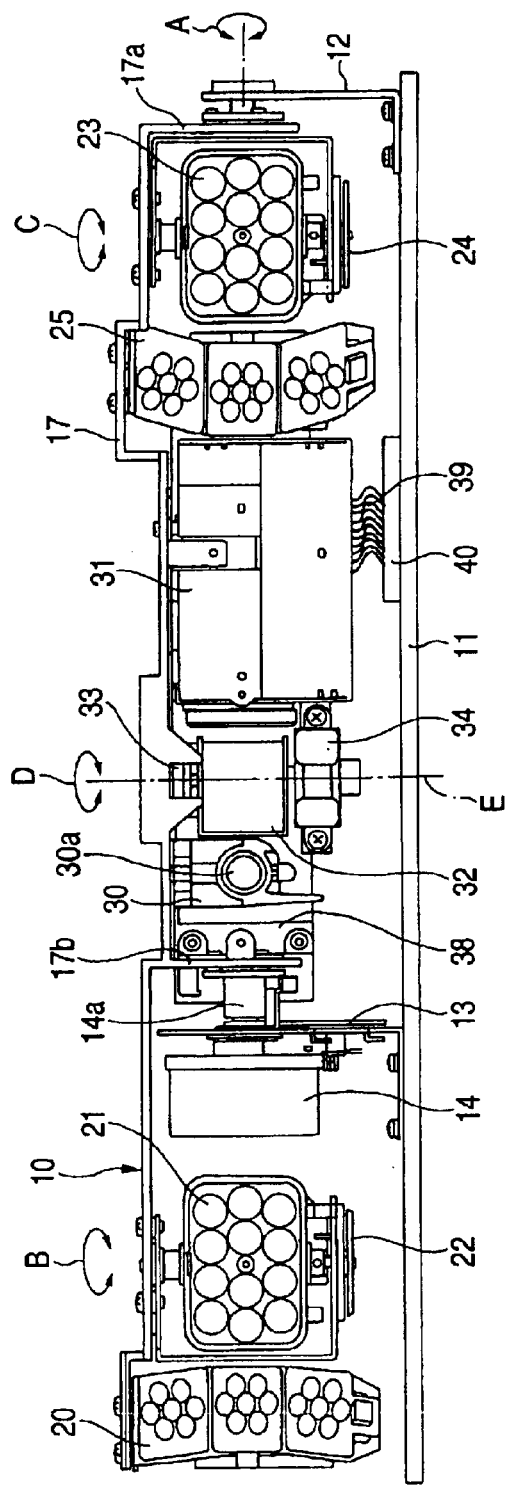
FIG. 1 is a front view illustrating the state that the external panel of the iris imaging apparatus in the first embodiment of the invention is removed.

The reference numeral 10 and 60 each refer to a iris imaging apparatus; 11 to platform; 14 to tilt motor; 17 to turning stage (tilt stage); 20 and 25 to fixed lighting device (lighting device for the wide angle camera); 21 and 23 to movable lighting device (lighting device for illuminating the iris); 22, 24 and 33 to pan motor; 30 to wide angle camera; 31 to telephoto camera; 32 to rotating mirror; 34 to range sensor; 39 to flexible flat cable; 50 and 52 to lighting device for illuminating the iris; and 51 and 53 to lighting device for the wide angle camera.

DETAILED DESCRIPTION OF THE PREFERRED EMBODIMENTS (First Embodiment)

FIG. 1 is a front view illustrating an iris imaging apparatus in a first embodiment of the invention. A panel disposed outside is omitted in FIG. 1. An iris imaging apparatus 10 in the embodiment has a longitudinal platform 11. On the platform 11, a support plate 12 is erected and fixed on the right end part, and a support plate 13 is erected and fixed at a predetermined position on the left side. A tilt motor 14 is fixed with the support plate 13. A shaft 14a of the tilt motor 14 is projected from the support plate 13 in the direction of the support plate 12.

A right end part 17a of a plate-shaped turning stage (hereafter, it is called "tilt stage" because it turns in the tilt direction in the embodiment) 17 is bent at the right angle and is rotatablly supported by the support plate 12. A support plate 17b shaped in one piece with the tilt stage 17 is disposed at a predetermined position on the left side of the tilt stage 17. The support plate 17b is fixed to the shaft 14a of the tilt motor 14. Therefore, the entire tilt stage 17 performs the tilt operation in the directions of double-headed arrow "A" in accordance with the rotation of the tilt motor 14. The tilt motor 14 may be mounted on the tilt stage 17 side and the shaft 14a may be fixed to the support plate 13.

A fixed lighting device 20 is mounted on the most left end part of the tilt stage 17 extending toward the left side beyond the tilt motor 14. A movable lighting device 21 is disposed on the inner side (center side) of the fixed lighting device 20. The fixed lighting device 20 is formed of a set of a plurality of infrared light emitting diodes, which is fixed to the tilt stage 17 so as to direct the luminous light to the face of a person to be authenticated (not shown) who stands at a predetermined position in front of the iris imaging apparatus 10. The movable lighting device 21 is also formed of a set of a plurality of infrared light emitting diodes, which is mounted on the tilt stage 17 rotatablly by a pan motor 22 in the directions of double-headed arrow "B".

Also at the end on the right side of the tilt stage 17, a movable lighting device 23 formed of a set of a plurality of infrared light emitting diodes is mounted rotatablly by a pan motor 24 in the directions of double-headed arrow "C". On the inner side (center side) of the movable lighting device 23, a fixed lighting device 25 formed of a set of a plurality of infrared light emitting diodes is fixed. The fixed lighting device 25 is fixed in the tilt stage 17 so as to direct the luminous light to the face of the person to be authenticated who stands at a predetermined position in front of the iris imaging apparatus 10, as similar to the fixed lighting device 20.

The fixed lighting devices 20 and 25 are allowed to emit light when a wide angle camera 30 images the face image of the person to be authenticated. The movable lighting devices 21 and 23 are allowed to emit light when a telephoto camera 31 images the enlarged image of the eye of the person to be authenticated. Therefore, a condenser lens is mounted at the position in front of each of the light emitting diodes of the movable lighting devices 21 and 23 so as to allow the luminous light to be gathered at the position of the eye. On the other hand, the condenser lens is not mounted in the fixed lighting devices 20 and 25 in order to illuminate a wider area.

The wide angle camera 30 and the telephoto camera 31 are fixed between the support plate 17 band the fixed lighting device 25 of the tilt stage 17. The wide angle camera 30 disposed adjacent to the support plate 17b is fixed to the tilt stage 17 so that an imaging lens 30a is directed to the person to be authenticated standing at a predetermined position in front of the iris imaging apparatus 10 and that the optical axis crosses the rotation axis of the double-headed arrow "A" of the tilt stage 17.

The telephoto camera 31 disposed adjacent to the fixed lighting device 25 is disposed transversely so that the lens optical axis is coaxial with the rotation axis of the double-headed arrow "A" of the tilt stage 17. A rotating mirror 32 is disposed between the wide angle camera 30 and the telephoto camera 31. The rotating mirror 32 reflects the light incident into the iris imaging apparatus 10 from the direction of the person to be authenticated to the telephoto camera 31.

The rotating mirror 32 is mounted on the tilt stage 17 rotatablly by a pan motor 33 in the directions of double-headed arrow "D". A range sensor 34 is fixed at the position below the rotating mirror 32 of the tilt stage 17. It is acceptable that the range sensor 34 is mounted on the rotating mirror 32 in one piece and is moved in association with the pan operation of the rotating mirror 32.

A switching substrate 38 is mounted between the support plate 17b and the wide angle camera 30. A flexible flat cable 39 routed around the backside of the wide angle camera 30, the rotating mirror 32 and the telephoto camera 31 is drawn from the switching substrate 38 at the position below the telephoto camera 31. The flexible flat cable is connected to a control device 40 disposed on the platform 11.

FIG. 2 is a block diagram illustrating an electrical system of the iris imaging apparatus described in FIG. 1. A double line in the drawing indicates a mechanical joining part, and thick solid lines are electrical wiring lines. A control microcomputer 41 and four motor drivers 42, 43, 44 and 45 are mounted on the switching substrate 38. The control microcomputer 41 controls the rotating direction and torque of the tilt motor 14 and each of the pan motors 22, 24 and 33 by sending control signals to each of the motor drivers 42, 43, 44 and 45. The control microcomputer 41 controls turning on and off of the fixed lighting devices 20 and 25 and the movable lighting devices 21 and 23. Furthermore, the control microcomputer 41 acquires measurement data from the range sensor 34 for autofocus control and imaging control of the wide angle camera 30 and the telephoto camera 31.

In the embodiment, the switching substrate 38 is mounted to the tilt stage 17, and the control microcomputer 41 on the switching substrate 38 controls all the subjects to be controlled such as the fixed lighting devices 20 and 21 disposed on the tilt stage 17. Accordingly, the electrical wiring lines connecting the control microcomputer 41 with each of the subjects to be controlled can be routed on the tilt stage 17. The connection of the control microcomputer 41 and the control device 40 can be implemented by the single flexible flat cable 39. Therefore, the complicated wiring lines does not hinder the tilt operation by the tilt stage 17.

The iris imaging apparatus 10 is disposed and fixed to the entrance of buildings and rooms at high levels of security or ATMs in banks, for example. When the control microcomputer 41 senses that a person to be authenticated enters into a image-taking bounds, that is, a predetermined position in front of the rotation axis"E" of the rotating mirror 32 by the detection signal of the range sensor 34, the wide angle camera 30 first images the image of the person to be authenticated. At this time, any one or both of the fixed lighting devices 20 and 25 are turned on.

The control microcomputer 41 captures and analyzes the image imaged by the wide angle camera 30, and determines the positions on the face of the person to be authenticated by pattern matching. When the control microcomputer 41 determines that the face image is not include in the image imaged by the wide angle camera 30, it controls the tilt motor 14 to set the face image in the center of the angle of view of the wide angle camera 30 and again turns on the fixed lighting devices 20 and 25 to image the face image.

At this time, as the fixed lighting devices 20 and 25 are mounted on the tilt stage 17, the luminous light is directed to the face of the person to be authenticated. Therefore, the person to be authenticated can be illuminated efficiently. In this manner, the orientation of the luminous light can be tilted without disposing a tilt motor exclusive to the fixed lighting devices 20 and 25. Therefore, the number of the light emitting diodes to be mounted on the fixed lighting devices 20 and 25 can be reduced, and the reduction in fabrication costs can be intended.

The control microcomputer 41 calculates the position of the eye image from the face image by pattern matching. The control microcomputer 41 controls the tilt motor 14 and each of the pan motors 22, 24 and 33 so that the orientation of the luminous light of the movable lighting devices 21 and 23 is directed to the eye of the person to be authenticated and that the telephoto camera 31 images the enlarged image of the eye of the person to be authenticated.

In the embodiment, since all the components required for the tilt operation are mounted on the tilt stage 17, a tilt motor exclusive to the movable lighting devices 21 and 23 does not need to be disposed. Consequently, the number of motors to be mounted on the iris imaging apparatus 10 is reduced, and the low cost, light weight and compact in size can be intended.

When the telephoto camera 31 images the enlarged image of the eye, one of the movable lighting devices 21 and 23 illuminates the iris of the person to be authenticated. For example, in the case that the movable lighting device 21 is reflected to the imaged image captured by being illuminated by the movable lighting device 21 and the iris image is hidden from the high luminance image of the movable lighting device 21, the image is unsuitable for the iris authentication. In the case, the movable lighting device 23 illuminates the eye of the person to be authenticated, and the telephoto camera 31 images the iris image in which the movable lighting device 23 is not reflected.

Furthermore, in the case that the lighting device is inevitably reflected to the iris image of the right eye, the telephoto camera 31 similarly images the iris image of the left eye. Although the right eye varies from the left eye in the iris image, both the right eye and the left eye are registered when the authentication code of the iris image is registered in an iris authentication processor. Therefore, a good iris image of any one of the eyes is enough.

The lengths from right end to left end of the conventional iris imaging apparatus are formed long so as not to reflect the iris lighting devices, which illuminates iris, in the iris image. The iris lighting devices are disposed near the both ends, and the optical axis of the light illuminating the iris is greatly shifted from the optical axis reflected by the rotating mirror 32 of the telephoto camera 31. Therefore, the distance between the rotation axis E of the rotating mirror 32 and the iris lighting device is expanded. Consequently, the distance between the person to be authenticated and the iris lighting device is expanded, which requires the iris lighting device to emit a large amount of infrared radiation.

However, in the iris imaging apparatus 10 of the embodiment, the distances between the rotation axis E of the rotating mirror 32 and the movable lighting devices 21 and 23 are reduced as short as possible. The distances between the person to be authenticated standing at a predetermined position in front of the iris imaging apparatus 10 and the movable lighting devices 21 and 23 are shortened. Therefore, the amount of light emitted from the movable lighting devices 21 and 23 can be made small. That is, as the number of the light emitting diodes can be reduced, the costs can be curtailed.

However, the optical axis of the luminous light for illuminating the iris comes close to the optical axis of the telephoto camera 31. Consequently, the high luminance images of the movable lighting devices 21 and 23 are highly likely to be reflected in the iris image. In the embodiment, the movable lighting device 21 and the movable lighting device 23 are disposed at asymmetrical positions with respect to the rotation axis E of the rotating mirror 32. The asymmetrical position results that the probability the high luminance image of the movable lighting device 23, one of them, is reflected in the iris image is reduced even if the high luminance image of the movable lighting device 21, the other of them, is reflected in the iris image. Accordingly, the probability that an good iris image can be imaged by any one of the movable lighting devices 21 and 23 becomes high.

The fixed lighting devices 20 and 25 are also disposed at asymmetrical positions with respect to the rotation axis E of the rotating mirror 32. Anyone or both of the fixed lighting devices 20 and 25 are allowed to emit light for imaging the iris image instead of the movable lighting devices 21 and 23 in the case where both of the movable lighting devices 21 and 23 are reflected in the iris image. Since the fixed lighting devices 20 and 25 for the wide angle camera are not disposed with the condenser lens, the probability that the high luminance image is reflected in the iris image is low. Accordingly, as the telephoto camera 31 has a high probability of capturing a good iris image, the width of the iris imaging apparatus 10 can be shortened.

The control microcomputer 41 sends data of the iris image to the control device 40 through the flexible flat cable 39 when an enlarged image of the iris imaged by the telephoto camera 31 is good in focus. The control device 40 performs the authentication process for the iris image. Alternatively, when the iris authentication processor is disposed inside a building, for example, not disposed in one piece with the iris imaging apparatus 10, the control device 40 sends data of the iris image or authentication code created from data of the iris image to the iris authentication processor through a cable not shown.

As described above, the width of the iris imaging apparatus is shortened to be compact. As the number of the light emitting diodes used for the lighting devices can be reduced, the fabrication costs can be curtailed. In addition, the tilt motor is shared to reduce the number of motors. Therefore, the entire apparatus can be compact in size, light weight and low cost.

The above-description explains that the range sensor 34 was fixed to the tilt stage 17, which allows the mounting structure of the range sensor 34 to be simple and allows the mounting costs to be reduced. The above-description also explains that the range sensor 34 at the correct position in the direction of the person to be authenticated allows highly accurate distance-measuring. However, even if the range sensor 34 is set not to be moved, the measurement errors are as small as they can be ignored in consideration of the depth of field.

To always dispose the range sensor 34 at a correct position with respect to the person to be authenticated in association with the rotation angle of the rotating mirror 32, the rotation angle of the range sensor 34 needs to be controlled so as to be twice as much as the rotation angle of the rotating mirror 32. However, the fabrication costs are increased when this is implemented by a link mechanism. The range sensor 34 is preferably fixed to the rotating mirror 32, as described above, in order to allow the range sensor 34 to move. In this case, although the rotation angle of the rotating mirror 32 is the same as that of the range sensor 34, the measurement errors are smaller than the case that the range sensor 34 is fixed to the tilt stage 17. It is enough in consideration of the cost increase when the link mechanism is disposed.

(Second Embodiment)

FIG. 3 is a front view illustrating an iris imaging apparatus in a second embodiment of the invention (in the state that an external panel is removed). The same components as those of the first embodiment shown in FIG. 1 are designated the same numerals and signs, omitting the description. In the first embodiment shown in FIG. 1, the fixed lighting devices 20 and 25 were fixed to the tilt stage 17. However, in the second embodiment, lighting devices 50 and 51 for the wide angle camera 30 can perform the pan operation.

The lighting device 50 for illuminating the iris is disposed to a pan motor 22. The lighting device 51 for the wide angle camera is also disposed to the surface shifted at an angle of 90 degrees on the left side with respect to the lighting device 50 of a pan motor 22. A lighting device 52 for illuminating the iris is disposed to a pan motor 24. A lighting device 53 for the wide angle camera is also disposed to the surface shifted at an angle of 90 degrees on the left side with respect to the lighting device 52 of a pan motor 24. It is the same as the first embodiment that a condenser lens is mounted at the position in front of each of the light emitting diodes for forming the lighting devices 50 and 52 for illuminating the iris and the condenser lens is not disposed for each of the light emitting diodes for forming the lighting devices 51 and 53 for the wide angle camera.

In the embodiment, the lighting devices 51 and 53 for the wide angle camera do not need to be turned on when the lighting devices 50 and 52 for illuminating the iris are turned on. The lighting devices 50 and 52 for illuminating the iris are not turned on when the lighting devices 51 and 53 for the wide angle camera are turned on. The iris imaging apparatus 60 of the embodiment is as follow in consideration of these.

When the wide angle camera 30 images the wide angle image of the person to be authenticated, a control microcomputer 41 controls a tilt motor 14 and the pan motors 22 and 24. The lighting devices 51 and 53 for the wide angle camera 30 are rotated in the left from the state shown in FIG. 3 to be in the state shown in FIG. 4 by the control of the control microcomputer 41 to be adjusted so as to direct the luminous light in the direction of the person to be authenticated. Then, a group of light emitting diodes of anyone or both of the lighting devices 51 and 53 for the wide angle camera emits infrared radiations in a wide area.

When a telephoto camera 31 images the enlarged image of the eye of the person to be authenticated, the pan motors 22 and 24 shown in FIG. 3 are controlled to radiate the infrared radiations gathered by the condenser lenses from any one of the lighting devices 50 and 52 to the eye of the person to be authenticated. In this manner, the lighting devices 51 and 53 for the wide angle camera can perform the pan operation and the tilt operation as well. Therefore, the number of the light emitting diodes of the lighting devices 51 and 53 for the wide angle camera can be further reduced.

In addition, in the embodiment shown in FIG. 3, the rotation axes of the pan motors 22 and 24 are disposed at positions in the same distance, that is, at symmetrical positions with respect to the rotation axis E of the rotating mirror 32. However, they are disposed at the asymmetrical positions as similar to the first embodiment, which can allow low probability that the iris lighting devices are reflected in the iris image as a high luminance image.

What is claimed is:

1. An iris imaging apparatus comprising:
   a telephoto camera for imaging an enlarged image of an eye of a person to be authenticated;
   a first iris lighting device controlled to emit light when the telephoto camera images the enlarged image;
   a iris lighting motor for rotating the first iris lighting device to set direction of light emitted from the first iris lighting device to a position of the eye of the person to be authenticated;
   a platform;
   a turning stage rotatably mounted on the platform, with which the telephoto camera, the first iris lighting device and the iris lighting motor are mounted;

a rotating mirror for reflecting an incident light from the eye of the person to be authenticated to the telephoto camera;

a rotating mirror motor for rotating the rotating mirror; and a range sensor for measuring distance to the person to be authenticated being provided to a position below the rotating mirror, wherein the rotating mirror and the rotating mirror motor are mounted with the turning stage, and the telephoto camera is disposed transversely so that the rotation axis of the turning stage is coaxial with an optical axis of the telephoto camera.

2. The iris imaging apparatus according to claim 1, further comprising:

a wide angle camera for imaging an image to determine the position of the eye of the person to be authenticated; and a wide angle camera lighting device controlled to emit light when the wide angle camera images, wherein the wide angle camera and the wide angle camera lighting device are mounted with the turning stage.

3. The iris imaging apparatus according to claim 2, further comprising:

a controller for controlling the wide angle camera lighting device to emit light and controlling the telephoto camera to image the iris image of the person to be authenticated when an image of the first iris lighting device is reflected in an iris image of the person to be authenticated imaged by the telephoto camera.

4. The iris imaging apparatus according to claim 1, wherein a rotation axis of a turn motor for turning the turning stage is set to the turning stage.

5. The iris imaging apparatus according to claim 1, wherein the range sensor is provided so as to rotate in one piece with the rotating mirror.

6. The iris imaging apparatus according to claim 1, wherein a substrate having a unit for controlling a subject to be electrically controlled is mounted on the turning stage.

7. The iris imaging apparatus according to claim 1, further comprising:

a second iris lighting device controlled to emit light when the telephoto camera images the enlarged image, wherein a first position where the first iris lighting device is provided is left side of the turning stage and a second position where the second iris lighting device is provided is right side of the turning stage, and the first position and the second position are asymmetric with respect to an optical axis of the telephoto camera directed to the person to be authenticated.

8. An iris imaging apparatus comprising:

a platform;

a wide angle camera for imaging an image of a person to be authenticated;

a wide angle camera lighting device controlled to emit light when the wide angle camera images;

a telephoto camera for imaging an enlarged image of an eye of the person to be authenticated;

an iris lighting device controlled to emit light when the telephoto camera images the enlarged image;

a first motor for rotating the iris lighting device to direct luminous light in a direction of the person to be authenticated;

a turning stage rotatably mounted on the platform, with which the wide angle camera, the wide angle camera lighting device, the telephoto camera, the iris lighting device and the first motor are mounted; and a second motor for turning the turning stage, wherein the wide angle camera lighting device and the iris lighting device are arranged side by side to be adjusted lighting direction by the first motor.

9. The iris imaging apparatus according to claim 8, further comprising:

a controller for controlling the second motor, and the wide angle camera, the wide angle camera lighting device, the telephoto camera, the iris lighting device and the first motor mounted on the turning stage, wherein the controller is mounted with the turning stage.

* * * * *